United States Patent [19]

Fukuda et al.

[11] Patent Number: 5,434,246
[45] Date of Patent: Jul. 18, 1995

[54] PARATHYROID HORMONE DERIVATIVES

[75] Inventors: Tsunehiko Fukuda, Kyoto; Shizue Nakagawa; Shigehisa Taketomi, both of Osaka, all of Japan

[73] Assignee: Takeda Chemical Industries, Ltd., Osaka, Japan

[21] Appl. No.: 33,099

[22] Filed: Mar. 16, 1993

[30] Foreign Application Priority Data

Mar. 19, 1992 [JP] Japan .................................. 4-063517
Feb. 18, 1993 [JP] Japan .................................. 5-029283

[51] Int. Cl.$^6$ ...................... C07K 14/00; C07K 4/00; A61K 38/23
[52] U.S. Cl. ........................................... 530/324
[58] Field of Search ............... 530/324; 930/DIG. 10; 514/12

[56] References Cited

U.S. PATENT DOCUMENTS

| | | | |
|---|---|---|---|
| 4,086,196 | 4/1978 | Tregear | 530/324 |
| 4,086,198 | 4/1978 | Tregear | 530/324 |
| 4,656,250 | 4/1987 | Morita et al. | 530/324 |
| 4,968,669 | 11/1990 | Rosenblatt | 514/12 |

FOREIGN PATENT DOCUMENTS

0477885A2 4/1992 European Pat. Off. .
WO92/00753 1/1992 WIPO .

OTHER PUBLICATIONS

Reeve et al., British Medical J., 7 Jun. pp. 1340–1344 (1980).
Lehninger, "Principles of Biochemistry", Worth Pub. pp. 100–101 (1982).
Biochemistry, 17(16):3188–3191 (1978).
F. Cohen et al., The Journal of Biological Chemistry, 266(3):1997–2004 (1991).

Primary Examiner—Howard E. Schain
Assistant Examiner—Phynn Touzeau
Attorney, Agent, or Firm—David G. Conlin; Peter F. Corless

[57] ABSTRACT

Parathyroid hormone (PTH) derivatives represented by the general formula:

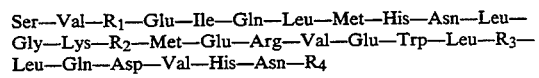

Ser—Val—$R_1$—Glu—Ile—Gln—Leu—Met—His—Asn—Leu—Gly—Lys—$R_2$—Met—Glu—Arg—Val—Glu—Trp—Leu—$R_3$—Leu—Gln—Asp—Val—His—Asn—$R_4$ or a salt thereof, wherein $R_1$ represents Ser or a D-α-amino acid residue of 4 or less carbon atoms;

$R_2$ represents a tetrapeptide chain which contains at least one water-soluble α-amino acid residue;

$R_3$ represents a tripeptide chain which contains at least one water-soluble α-amino acid residue; and $R_4$ represents an aromatic amino acid residue or an amide thereof, except that $R_1$ is Ser when $R_2$ is His-Leu-Asn-Ser, $R_3$ is E-F-G wherein E is Arg or His, F is Lys or His, G is Lys, Leu or Gln, are disclosed.

The parathyroid hormone derivatives of the present invention are stable and have high biological activity, therefore they are useful as drugs for bone diseases and the like.

23 Claims, No Drawings

PARATHYROID HORMONE DERIVATIVES

BACKGROUND OF THE INVENTION

The present invention relates to novel parathyroid hormone derivatives useful in hormone therapy.

Parathyroid hormone (PTH) is synthesized in the parathyroid, and plays an important role in controlling blood calcium concentrations or phosphoric acid ion concentrations by acting on the bone and the kidney which are its target organs. PTH is a peptide hormone consisting of 84 amino acids, and the biological activity thereof can be reproduced by a peptide fragment of an N-terminal (1 through 34 amino acid) portion [G. W. Tregear et al, *Endocrinology* 93, 1349–1353 (1973)].

The amino acid sequence of the peptide fragment of the N-terminal (1 through 34 amino acid) portion of this human type PTH (this peptide fragment is hereinafter abbreviated as human PTH(1–34)) is as follows:

```
 1    2    3    4    5    6    7    8    9    10   11   12   13
H—Ser—Val—Ser—Glu—Ile—Gln—Leu—Met—His—Asn—Leu—Gly—Lys—

14   15   16   17   18   19   20   21   22   23   24   25   26
His—Leu—Asn—Ser—Met—Glu—Arg—Val—Glu—Trp—Leu—Arg—Lys—

27   28   29   30   31   32   33   34
Lys—Leu—Gln—Asp—Val—His—Asn—Phe—OH     (SEQ ID NO: 1)
```

From the biological action of PTH, it is expected that the use of PTH as a drug will provide a drug useful for various bone diseases and the like. However, the following properties of the peptide are obstacles to its efficacious use as a therapeutic agent:

(1) The peptide is easily decomposed by various enzymes within the body;

(2) The absorption efficiency of the peptide into the body through various routes is very low; and (3) The peptide is unstable to various physico-chemical conditions such as oxidation.

In order to solve such problems and understand the relationship between structure and activity of the above hormone, various derivatives have been synthesized for the PTH(1–34) fragment. While a number of syntheses have been conducted for bovine PTH(1–34), few examples are known for human PTH(1–34). For example in one such derivatives, when the C-terminus Phe of human PTH(1–34) is converted to Phe-NH$_2$, an increase in activity is observed (Japanese Patent Unexamined Publication No. 58-96052). This increase in activity is believed to be due to inhibition of carboxypeptidase which decomposes the hormone. Further, human PTH(1–34) contains two Met residues. A molecule in which these residues are substituted with Nle residues prevents the hormone from losing its activity due to oxidation (Japanese Patent Unexamined Publication No. 61-24598).

Furthermore, F. E. Cohen et al. substituted the 3-position Ser of bovine PTH(1–34) with various L-amino acids, but the activity was markedly reduced by the amino acid substitution, except that the Ala substituted peptide exhibited an activity approximately similar to that of the natural type peptide [*The Journal of Biological Chemistry* 226, 1997–2004 (1991)]. S. Reppe et al. showed that for the human PTH(1–84) protein in which the 26-position Lys was substituted with Gln, the protein had an activity similar to that of the natural type protein [*The Journal of Biological Chemistry* 226, 14198–14201 (1991)]. As to the active human PTH(1–34) fragment, however, no derivative similarly substituted has been known.

SUMMARY OF THE INVENTION

In order to solve the above described problems, the inventors previously substituted one or more amino acid residues of human PTH(1–34) by chemical synthesis and proposed several human PTH(1–34) derivatives by (1) amino acid residue substitution considering the resistance to various proteases, (2) enhancement in activity of the hormone according to the amino acid residue substitution considering the expected two-dimensional structure as well as hydrophilic/hydrophobic or ionic media, and (3) substitution of the amino acid residue unstable to acidic, basic or oxidation conditions with an amino acid residue stable to these conditions (European Patent Publication No. 477885). As a result of further intensive investigation, the inventors have now discovered that substitution of the 3-position, 14-position, 15-position, 16-position, 17-position, 25-position, 26-position, 27-position or 34-position amino acid, or combinations thereof provide peptide derivatives having excellent activity.

In particular, the present invention provides a peptide represented by the amino acid sequence:

Ser—Val—R$_1$—Glu—Ile—Gln—Leu—Met—His—Asn—Leu—Gly—Lys—R$_2$—Met—Glu—Arg—Val—Glu—Trp—Leu—R$_3$—Leu—Gln—Asp—Val—His—Asn—R$_4$ or a salt thereof wherein R$_1$ represents Ser or a D-α-amino acid residue of 4 or less carbon atoms;

R$_2$ represents a tetrapeptide chain which contains at least one water-soluble α-amino acid residue;

R$_3$ represents a tripeptide chain which contains at least one water-soluble α-amino acid residue; and R$_4$ represents an aromatic amino acid residue or an amide thereof, except that R$_1$ is Ser when R$_2$ is His-Leu-Asn-Ser, R$_3$ is E-F-G wherein E is Arg or His, F is Lys or His, G is Lys, Leu or Gln.

DESCRIPTION OF THE INVENTION

In the present specification, a water-soluble α-amino acid means a naturally occurring or non-natural type hydrophilic α-amino acid which has a polar group at the side chain. A naturally occurring water-soluble α-amino acid is especially preferable. Among them, the naturally occurring amino acid means a water-soluble amino acid constituting a natural protein originating from animals, plants or microorganisms and an amino acid which is a metabolite thereof. They may be acidic-, neutral- and basic- amino acid depending on the polar groups such as a carboxyl, amino, guanidino, carboxamide, imidazole and hydroxyl group at the side chain.

The basic amino acid residue is preferablly an L- or D-α amino acid residue represent by the following formula:

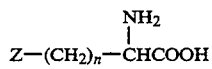

wherein Z represents NH$_2$, NHC(NH)NH$_2$ or an imidazole ring, n represents the integer of 1 to 5.

Examples of the D-α-amino acids of 4 or less carbon atoms represented by R$_1$ include neutral amino acids such as D-Ala, D-Asn, D-Cys, D-Ser and D-Thr, and preferably D-α-amino acids of 3 or less carbon atoms such as D-Ser and D-Ala.

When R$_2$ of a tetrapeptide chain having at least one water-soluble amino acid is represented by A-B-C-D, A represents His or a water-soluble amino acid other than His; B represents Leu or a water-soluble amino acid; C represents Asn or a water-soluble amino acid other than Asn; and D represents Ser or a water-soluble amino acid other than Ser.

A water-soluble amino acid in A,B,C,D of R$_2$ includes D- or L-Lys, Gln, Asp, Glu, Thr, Asn, Arg, Ser, His, ornithine, homoarginine 2,3-diaminopropionic acid and Gly, among them Lys and Arg is preferable.

Any combination of A, B, C and D of R$_2$ can be employed and preferable combinations include His-Lys-Lys-Lys, His-Leu-Lys-Lys, Lys-Lys-Lys-Lys and His-Leu-Lys-Ser.

In R$_3$, a tripeptide chain E-F-G having at least one water-soluble amino acid residue, a preferable amino acid is a neutral or basic amino acid. The neutral amino acid residue includes Ser, Asn, Gln, Thr, Gly, Cit and Hci. The basic amino acid residue includes Arg, Lys, His, ornithine, homoarginine, 2,3-diaminopropionic acid, 2,4-diaminobutyric acid, 2-amino-4-guanidino-butyric acid, 2-amino-3-guanidino-propionic acid.

Any combination of E, F and G of R$_3$ can be employed, and Arg-Gln-Gln and Arg-Lys-His are most preferable R$_4$, an aromatic amino acid residue or an amide thereof includes Phe, Phe-NH$_2$, Tyr and Tyr-NH$_2$.

Substitution in PTH(1-34) fragment may be not only at one position but also at two or more positions by a combination of R$_1$, R$_2$, R$_3$ and R$_4$. The substitution combination up to four positions is practical, as will be described in the following examples. Especially in the case of substitution at 3rd or 34th position, combination with other substitution at other position is preferable.

Peptide synthesis in the present invention can be carried out by the use of an automatic peptide synthesizer. The method of R. B. Merrifield [*Advances in Enzymology* 32, 221-296 (1969)] applies correspondingly to a basic synthesis course. In this method, the amino acid of the carboxyl terminus is covalently bound to a resin carrier, and elimination of a protective group of an α-amino group and condensation of a protected amino acid are repeated in turn to extend a peptide chain to the amino terminus, thereby obtaining a protected peptide resin having a desired amino acid sequence. This method is based on the above-described principle. The condensation of each amino acid and the elimination of the protective groups of the α-amino groups are performed under approximately similar conditions, and purification of intermediates is not conducted. Peptides of this invention may be rapidly synthesized by this method, so that this method is very convenient to synthesize various peptides. The protected peptide resin thus obtained is reacted with, for example, anhydrous hydrogen fluoride, trifluoromethanesulfonic acid or trifluoroacetic acid in the coexistence of various additives, whereby elimination of the peptide from the resin and removal of all protective groups can be achieved in one step.

The resulting crude peptide can be purified by known means for purifying peptides or proteins. Examples of such means include column chromatography under various principles such as gel filtration, ion exchange chromatography using a cation exchange resin or an anion exchange resin, hydrophobic chromatography and partition adsorption chromatography, and high performance liquid chromatography(HPLC).

The peptides of the present invention can be obtained in various salt forms. Examples of the salts include salts of inorganic acids, salts of organic acids such as formic acid, acetic acid, tartaric acid and citric acid, salts of inorganic bases such as sodium and ammonium, and salts of organic bases such as triethylamine, ethylamine and methylamine.

The human PTH(1-34) derivative peptides represented by the general formula of the present invention can be used as therapeutic agents for osteoporosis, hypoparathyroidism and hypertension. The forms thereof include injections, nasotracheal absorption agents, perrectum absorption agents, transvaginal absorption agents, percutaneous absorption agents and eye drops. In some cases, they are orally administered.

When the peptides are used as such therapeutic agents, effective amounts thereof are used to treat mammals especially human. Although they are generally used within the range of 1 ng to 100 μg/kg of weight, precise amounts thereof may be determined by those skilled in the art.

When the peptides are used as the therapeutic agents, they must be carefully purified so as to contain no bacteria and no pyrogens. Such purification may be performed according to methods known in the art.

The peptides, when used as the therapeutic agents for osteoporosis and the like, can be administered parenterally in the form of the above-described injections, nasotracheal absorption agents, perrectum absorption agents, transvaginal absorption agents, percutaneous absorption agents or eye drops, solely or in combination with pharmaceutically acceptable carriers, excipients or diluents. In the case of the injections, it is appropriate that the peptides are given to adults in a dose of 50 ng/kg to 5 mg/kg for 1 to 3 days, and preferably in a dose of 1 to 500 μg/kg for 1 to 3 days. For the injections, it is appropriate that the concentration of the therapeutic agents is 10 to 100 μg/ml.

When amino acids and the like are indicated by abbreviations in this specification, the abbreviations adopted by the IUPAC-IUB Commission on Biochemical Nomenclature or those commonly used in the art are employed. For example, the following abbreviations are used. When the amino acids are capable of existing as optical isomers, it is understood that the L-forms are represented unless otherwise specified.

Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine
Nle: Norleucine
Cit: Citrulline
Hci: Homocitrulline
Orn: Ornithine
hPTH: Human PTH By the amino acid substitution in the PTH(1-34) as described above, the resistance to various proteases is increased and the persistence of the activity in blood is obtained. This is achieved by, for example, substituting the D-α-amino acids for the 3-position of PTH(1-34). Further, high PTH activity was expressed by the substitution of at least one of the 14th to 17th-position with other water-soluble α-amino acid(s), especially with amino acid(s). Furthermore, it was observed that activity was also maintained or increased by the substitution of at least one of the 25-position to 27-position basic amino acids with water-soluble α-amino acid(s) espesially other neutral or basic amino acid(s)

EXAMPLES

The present invention will hereinafter be described in detail with the following examples. It is understood of course that the typical examples of amino acid substitution are not intended to limit the scope of the invention.

EXAMPLE 1

Synthesis and Purification of PTH (1-34) Fragment Derivatives

The peptides were synthesized in accordance with a modified method of the solid phase peptide synthesis developed by R. B. Merrifield et al., *Adv. Enzymol.* 32, 221-296 (1969), and an automatic peptide synthesizer 430A (Applied Biosystems) was used. Protected peptide-resins were synthesized using protocols specified by Applied Biosystems. Protected amino acid-p-oxymethylphenylacetoamidomethyl resins (polystyrene-1% divinylbenzene) are used as starting materials when derivatives having free carboxylic acids as carboxyl termini are desired, and 4-methylbenzhydryl resins are used as starting materials when derivatives of carboxylamides are desired, and protected amino acids were condensed thereto successively. In order to protect an α-amino group of each amino acid on condensation, a tertiary butyloxycarbonyl (BOC) group was used. Side functional groups were protected in the following manner. Hydroxyl groups of serine and threonine were protected as O-benzyl ethers, a hydroxyl group of tyrosine as a p-bromobenzyloxycarbonyl ester, carboxyl groups of glutamic acid and aspartic acid as benzyl esters, imidazole nitrogen of histidine with benzyloxymethyl, a side chain amino group of lysine with 2-chlorobenzyloxycarbonyl, a side chain amino group of ornithine with benzyloxycarbonyl, a guanidine functional group of arginine with a p-toluenesulfonyl group, and indoleimine of tryptophan with a formyl group. All amino acids were obtained from Applied Biosystems Japan, Nova Biochem and Bachem Chemicals.

After all of the amino acids were condensed on the resin, the protected peptide resin was taken out of the synthesizer and dried. The peptide resin (1 g) was allowed to react with anhydrous hydrogen fluoride (8 ml) containing p-cresol (1 ml), 1,2-ethanedithiol (1 ml) and 2-mercaptopyridine (100 mg) at 0° C. for 2 hours. After completion of reaction, hydrogen fluoride was removed by distillation and the residue was washed with diethyl ether to remove most of additives. The peptide was extracted with 3% acetic acid (10 ml), and the resin was removed by filtration. The filtrate was purified by gel filtration using a Sephadex G-25 column. The conditions of gel filtration were as follows: column size: 2.8×60 cm; detecting wavelength: 230 or 280 nm; solvent: 3% acetic acid; flow rate: 40 ml/hour. Fractions containing the peptide were collected and then lyophilized. The resulting powder sample was further purified by reversed phase high performance liquid chromatography [column: YMC-pack, A-324 ODS (10×250 mm); eluting solvent A: 0.1% trifluoroacetic acid-99.9% water; eluting solvent B: 0.1% trifluoroacetic acid-99.9% acetonitrile; linear gradient elution program: 0 minute (90% A+10% B), 30 minutes (60% A+40% B) (if necessary another elution program may sometimes be used); elution rate: 1.6 ml/minute; detecting wavelength: 230 or 280 nm]. Peak fractions containing the desired pure product were collected, and passed through a Bio RAD AGIX8 column (acetate form, 1.8×5 cm). The eluate was combined with the washings, and acetonitrile was removed therefrom by distillation, followed by lyophilization.

The peptides thus obtained, the results of amino acid analysis thereof, and the retention times on reversed phase high performance liquid chromatography are shown in Table In Table 1, a, b and c are as follows:

a: The peptides were hydrolyzed in tubes sealed with 6 N hydrochloric acid under reduced pressure, in the presence of 4% thioglycolic acid at 110° C. for 24 hours, and then subjected to amino acid analysis. Theoretical values are designated in parentheses.

b: Names of test compounds (no NH$_2$ at the terminus means COOH):

(1) [D-Ser$^3$]hPTH(1-34)NH$_2$
(2) [D-Ala$^3$]hPTH(1-34)
(3) [Thr$^{16}$]hPTH(1-34)
(4) [Glu$^{16}$]hPTH(1-34)
(5) [Lys$^{16}$]hPTH(1-34)
(6) [Thr$^{27}$]hPTH(1-34)
(7) [Asn$^{27}$]hPTH(1-34)
(8) [Gln$^{26,27}$]hPTH(1-34)
(9) [Gln$^{25,26,27}$]hPTH(1-34)
(10) [Ser$^{27}$]hPTH(1-34)
(11) [Gly$^{27}$]hPTH(1-34)
(12) [His$^{27}$]hPTH(1-34)
(13) [Lys$^{16}$,Gln$^{27}$]hPTH(1-34)
(14) [Orn$^{16}$,Gln$^{27}$]hPTH(1-45)
(15) [Hci$^{16}$,Gln$^{27}$]hPTH(1-34)
(16) [Asp$^{16}$,Gln$^{27}$]hPTH(1-34)
(17) [Arg$^{16}$,Gln$^{27}$]hPTH(1-34)
(18) [Arg$^{26,27}$]hPTH(1-34)
(19) [Gln$^{26}$]hPTH(1-34)
(20) [Lys$^{15,16}$,His$^{27}$]hPTH(1-34)
(21) [Lys$^{15}$,His$^{27}$]hPTH(1-34 )
(22) [Gln$^{25}$]hPTH(1-34)
(23) [D-Lys$^{16}$]hPTH(1-34)
(24) [Lys$^{15,16,17}$,His$^{27}$]hPTH(1-34)

(25) [Gln¹⁶]hPTH(1-34)
(26) [Ser¹⁶]hPTH(1-34)
(27) [Gly¹⁶]hPTH(1-34)
(28) [Lys¹⁶]hPTH(1-34)NH₂
(29) [Lys¹⁶Asp¹⁷]hPTH(1-3)
(30) [Lys¹⁴,¹⁵,¹⁶,¹⁷]hPTH(1-34)
(31) [Lys¹⁵,¹⁶,¹⁷]hPTH(1-34)
(32) [Lys¹⁶,¹⁷]hPTH(1-34)
(33) [Arg¹⁶,¹⁷]hPTH(1-34)
(34) [Arg¹⁵,¹⁶,¹⁷]hPTH(1-34)

c: Retention time of the peptides by high performance liquid chromatography

Analysis conditions: a VISTA 5000 high performance chromatogram (Varian) linked to a 712 W autosampler (Waters) was used. Column: YMC A-324 ODS (4.6×250 mm); eluent A: 0.1% trifluoroacetic acid-99.9% water; eluent B: 0.1% trifluoroacetic acid-99.9% acetonitrile; linear gradient elution program: 0 minute (80% A+20% B), 30 minutes (50% A+50% B); flow rate: 0.7 ml/minute; detecting wavelength: 280 nm]

TABLE 1

Amino Acid Composition of PTH(1-34) Derivatives (a) Derivative Peptide (b)

| Amino Acid | (1) | (2) | (3) | (4) | (5) |
|---|---|---|---|---|---|
| Asx | 4.00(4) | 4.00(4) | 3.00(3) | 3.00(3) | 3.00(3) |
| Ser | 2.37(3) | 1.73(2) | 2.32(3) | 2.59(3) | 2.57(3) |
| Glx | 4.91(5) | 5.07(5) | 5.02(5) | 6.11(6) | 5.04(5) |
| Gly | 1.02(1) | 0.97(1) | 1.00(1) | 0.98(1) | 0.99(1) |
| Val | 2.64(3) | 2.73(3) | 2.66(3) | 2.78(3) | 2.72(3) |
| Met | 1.80(2) | 1.88(2) | 2.04(2) | 2.15(2) | 2.14(2) |
| Ile | 0.78(1) | 0.89(1) | 0.93(1) | 0.89(1) | 0.87(1) |
| Leu | 4.95(5) | 5.08(5) | 5.00(4) | 5.08(5) | 5.05(5) |
| Phe | 1.08(1) | 0.99(1) | 1.00(2) | 1.01(1) | 1.01(1) |
| Lys | 3.02(3) | 3.07(3) | 2.92(3) | 2.93(3) | 3.91(4) |
| His | 3.03(3) | 2.61(3) | 2.54(3) | 2.72(3) | 2.71(3) |
| Trp | 0.94(1) | 0.85(1) | 0.87(1) | 0.90(1) | 0.86(1) |
| Arg | 2.01(2) | 1.90(2) | 1.94(2) | 1.94(2) | 1.93(2) |
| Other amino acids | | Ala 0.94(1) | Thr 0.86(1) | | |
| HPLC retention time (minute) (c) | 25.0 | 25.1 | 26.6 | 27.2 | 25.7 |

| Amino Acid | (6) | (7) | (8) | (9) | (10) |
|---|---|---|---|---|---|
| Asx | 4.00(4) | 5.00(5) | 4.00(4) | 4.00(4) | 4.00(4) |
| Ser | 2.52(3) | 2.61(3) | 2.60(3) | 2.62(3) | 3.67(4) |
| Glx | 5.12(5) | 5.12(5) | 7.02(7) | 8.03(8) | 5.09(5) |
| Gly | 0.92(1) | 0.95(1) | 0.99(1) | 1.01(1) | 1.04(1) |
| Val | 2.75(3) | 2.79(3) | 2.81(3) | 2.61(3) | 2.81(3) |
| Met | 1.69(2) | 1.72(2) | 2.04(2) | 2.05(2) | 1.91(2) |
| Ile | 0.88(1) | 0.89(1) | 0.93(1) | 0.91(1) | 0.94(1) |
| Leu | 4.92(5) | 4.98(5) | 5.01(5) | 5.00(5) | 4.89(5) |
| Phe | 1.05(1) | 1.05(1) | 1.02(1) | 1.02(1) | 0.96(1) |
| Lys | 1.91(2) | 1.92(2) | 0.96(1) | 0.91(1) | 1.92(2) |
| His | 2.60(3) | 2.63(3) | 2.68(3) | 2.68(3) | 2.46(3) |
| Trp | 0.92(1) | 0.89(1) | 0.92(1) | 1.04(1) | 0.93(1) |
| Arg | 1.89(2) | 1.89(2) | 1.90(2) | 0.92(1) | 1.89(2) |
| Other amino acids | Thr 0.91(1) | | | | |
| HPLC retention time (minute) (c) | 26.8 | 25.4 | 26.4 | 25.8 | 27.0 |

| Amino Acid | (11) | (12) | (13) | (14) | (15) |
|---|---|---|---|---|---|
| Asx | 4.00(4) | 4.00(4) | 3.00(3) | 3.00(3) | 3.00(3) |
| Ser | 2.59(3) | 2.55(3) | 2.71(3) | 2.63(3) | 2.66(3) |
| Glx | 5.05(5) | 5.02(5) | 6.20(6) | 6.15(6) | 6.20(6) |
| Gly | 2.03(2) | 1.01(1) | 1.02(1) | 1.01(1) | 1.00(1) |
| Val | 2.88(3) | 2.89(3) | 2.86(3) | 2.80(3) | 2.83(3) |
| Met | 1.94(2) | 1.94(2) | 1.98(2) | 2.04(2) | 2.03(2) |
| Ile | 1.01(1) | 0.98(1) | 0.93(1) | 0.90(1) | 0.92(1) |
| Leu | 4.98(5) | 4.94(5) | 5.06(5) | 5.03(5) | 5.03(5) |
| Phe | 1.00(1) | 1.01(1) | 1.02(1) | 1.00(1) | 1.00(1) |
| Lys | 1.96(2) | 1.93(2) | 2.97(3) | 1.85(2) | 2.23(2) |
| His | 2.75(3) | 3.66(4) | 2.77(3) | 2.80(3) | 2.80(3) |
| Trp | 0.99(1) | 0.97(1) | 0.98(1) | 0.99(1) | 0.93(1) |
| Arg | 1.91(2) | 1.92(2) | 1.92(2) | 1.95(2) | 1.96(2) |

TABLE 1-continued

Amino Acid Composition of PTH(1-34) Derivatives (a) Derivative Peptide (b)

| Other amino acids | | | | Orn 0.95(1) | |
|---|---|---|---|---|---|
| HPLC retention time (minute) (c) | 25.0 | 23.6 | 25.8 | 25.8 | 28.2 |

| Amino Acid | (16) | (17) | (18) | (19) | (20) |
|---|---|---|---|---|---|
| Asx | 4.00(4) | 3.00(3) | 4.00(4) | 4.00(4) | 3.00(3) |
| Ser | 2.41(3) | 2.43(3) | 2.67(3) | 2.76(3) | 2.57(3) |
| Glx | 5.97(6) | 5.87(6) | 5.12(5) | 6.23(6) | 5.11(5) |
| Gly | 0.91(1) | 0.92(1) | 1.06(1) | 1.13(1) | 1.03(1) |
| Val | 2.62(3) | 2.63(3) | 2.85(3) | 2.90(3) | 2.75(3) |
| Met | 1.81(2) | 1.87(2) | 1.97(2) | 1.98(2) | 1.88(2) |
| Ile | 0.78(1) | 0.82(1) | 0.95(1) | 0.97(1) | 0.95(1) |
| Leu | 4.76(5) | 4.74(5) | 4.89(5) | 4.97(5) | 4.05(4) |
| Phe | 0.94(1) | 0.95(1) | 0.98(1) | 1.00(1) | 1.04(1) |
| Lys | 1.81(2) | 1.84(2) | 0.95(1) | 1.92(2) | 3.75(4) |
| His | 2.53(3) | 2.61(3) | 2.86(3) | 2.81(3) | 3.62(4) |
| Trp | 0.87(1) | 0.77(1) | 0.79(1) | 0.77(1) | 0.63(1) |
| Arg | 1.61(2) | 2.77(3) | 3.83(4) | 1.93(2) | 1.84(2) |
| Other amino acids | | | | | |
| HPLC retention time (minute) (c) | 26.4 | 26.2 | 24.8 | 25.5 | 21.6 |

| Amino Acid | (21) | (22) | (23) | (24) | (25) |
|---|---|---|---|---|---|
| Asx | 4.00(4) | 4.00(4) | 3.00(3) | 3.00(3) | 3.00(3) |
| Ser | 2.57(3) | 2.59(3) | 2.39(3) | 1.62(2) | 2.69(3) |
| Glx | 5.18(5) | 6.09(6) | 4.88(5) | 5.12(5) | 6.22(6) |
| Gly | 1.06(1) | 1.07(1) | 0.98(1) | 1.02(1) | 1.03(1) |
| Val | 2.64(3) | 2.82(3) | 2.58(3) | 2.77(3) | 2.77(3) |
| Met | 1.87(2) | 1.99(2) | 1.85(2) | 1.86(2) | 2.19(2) |
| Ile | 0.93(1) | 0.92(1) | 0.80(1) | 0.97(1) | 0.94(1) |
| Leu | 4.03(4) | 4.86(5) | 4.82(5) | 4.03(4) | 5.00(5) |
| Phe | 1.04(1) | 1.00(1) | 0.98(1) | 1.05(1) | 1.03(1) |
| Lys | 2.79(3) | 2.69(3) | 3.76(4) | 4.76(5) | 2.87(3) |
| His | 3.61(4) | 2.80(3) | 2.59(3) | 3.62(4) | 2.68(3) |
| Trp | 0.73(1) | 0.73(1) | 0.89(1) | 0.81(1) | 0.92(1) |
| Arg | 1.85(2) | 1.03(1) | 1.86(2) | 1.84(2) | 1.87(2) |
| Other amino acids | | | | | |
| HPLC retention time (minute) (c) | 21.9 | 24.0 | 22.8 | 20.0 | 23.9 |

| Amino Acid | (26) | (27) | (28) | (29) | (30) |
|---|---|---|---|---|---|
| Asx | 3.00(3) | 3.00(3) | 3.00(3) | 4.00(4) | 3.00(3) |
| Ser | 3.35(4) | 2.50(3) | 2.59(3) | 1.71(2) | 1.76(2) |
| Glx | 5.09(5) | 5.14(5) | 4.98(5) | 5.02(5) | 5.20(5) |
| Gly | 0.95(1) | 1.89(2) | 0.99(1) | 1.00(1) | 1.00(1) |
| Val | 2.54(3) | 2.55(3) | 2.66(3) | 2.75(3) | 2.79(3) |
| Met | 1.77(2) | 1.79(2) | 1.84(2) | 1.89(2) | 2.11(2) |
| Ile | 0.86(1) | 0.86(1) | 0.87(1) | 0.89(1) | 0.93(1) |
| Leu | 5.13(5) | 5.20(5) | 5.03(5) | 4.89(5) | 4.05(4) |
| Phe | 1.08(1) | 1.08(1) | 1.04(1) | 0.99(1) | 1.05(1) |
| Lys | 2.74(3) | 2.81(3) | 3.65(4) | 3.88(4) | 6.90(7) |
| His | 2.53(3) | 2.55(3) | 2.63(3) | 2.49(3) | 1.72(2) |
| Trp | 0.85(1) | 0.80(1) | 0.85(1) | 0.90(1) | 0.92(1) |
| Arg | 1.93(2) | 1.94(2) | 1.89(2) | 1.88(2) | 1.96(2) |
| Other amino acids | | | | | |
| HPLC retention time (minute) (c) | 19.2 | 19.0 | 23.4 | 23.4 | 19.8 |

| Amino Acid | (31) | (32) | (33) | (34) |
|---|---|---|---|---|
| Asx | 3.00(3) | 3.00(3) | 3.00(3) | 3.00(3) |
| Ser | 1.74(2) | 1.63(2) | 1.73(2) | 1.77(2) |
| Glx | 5.15(5) | 5.07(5) | 5.11(5) | 5.07(5) |
| Gly | 1.00(1) | 0.95(1) | 1.00(1) | 1.01(1) |
| Val | 2.71(3) | 2.72(3) | 2.75(3) | 2.70(3) |
| Met | 2.09(2) | 1.96(2) | 2.11(2) | 2.10(2) |
| Ile | 0.90(1) | 0.86(1) | 0.91(1) | 0.91(1) |
| Leu | 4.01(4) | 4.93(5) | 5.01(5) | 3.98(4) |
| Phe | 1.06(1) | 1.05(1) | 1.03(1) | 1.03(1) |
| Lys | 5.90(6) | 4.85(5) | 2.89(3) | 2.89(3) |
| His | 2.61(3) | 2.50(3) | 2.56(3) | 2.52(3) |
| Trp | 0.94(1) | 0.89(1) | 0.95(1) | 0.95(1) |
| Arg | 1.96(2) | 1.96(2) | 3.84(4) | 4.73(5) |

TABLE 1-continued

| Amino Acid Composition of PTH(1-34) Derivatives (a) Derivative Peptide (b) | | | | |
|---|---|---|---|---|
| Other amino acids | | | | |
| HPLC retention time (minute) (c) | 19.4 | 22.7 | 23.2 | 20.0 |

EXAMPLE 2

Assay of Biological Activity of PTH (1-3) Derivatives

The biological activity of the PTH (1-34) derivatives was evaluated by a modified version of the method reported by Shigeno et al. in *The Journal of Biological Chemistry* 263, 18369-18377 (1988). A culture solution (Hank's solution, containing 20 mM N-2-hydroxyethyl-piperazine-N'-2-ethanesulfonic acid-(HEPES), 0.1% bovine serum albumin and 0.5 mM isobutylmethyl-xanthine) containing a 0.01, 0.1, 1, 10 or 100 nM derivative was added in an amount of 100 μl to a mouse cranial bone-derived osteoblast-like cell strain, MC3T3-EI cells, cultivated on a 96-well multiplate (Nunclon, Nunc), followed by reaction at room temperature for 30 minutes. After addition of 100 μl of 0.2N hydrochloric acid, the mixture was immersed in boiling water for 2.5 minutes, and cyclic adenosine monophosphate (cAMP) produced by a PTH receptor was extracted from the cells. The total cAMP in the culture solution and the cells was assayed using a commercial radioimmunoassay kit (cyclic AMP [$^{125}$I] kit "Du Pont-Daiichi", Daiichi Kagaku Yakuhin). An increase in cAMP production depending on the concentration of the human PTH (1-34) added as a standard was observed in each case. The biological activity of the PTH (1-34) derivatives is shown in Table 2.

TABLE 2

| Biological Activity of PTH (1-34) Analogues [Represented by Relative Activity to hPTH(1-34)] | |
|---|---|
| hPTH(1-34) | 1.00 |
| [D-Ala$^3$]hPTH(1-34) | 2.17 |
| [Thr$^{16}$]hPTH(1-34) | 1.74 |
| [Glu$^{16}$]hPTH(1-34) | 1.55 |
| [Lys$^{16}$]hPTH(1-34) | 3.37 |
| [Thr$^{27}$]hPTH(1-34) | 0.96 |
| [Gln$^{26,27}$]hPTH(1-34) | 1.19 |
| [Gln$^{25,26,27}$]hPTH (1-34) | 0.41 |
| [Orn$^{16}$,Gln$^{27}$]hPTH(1-34) | 1.82 |
| [Hci$^{16}$,Gln$^{27}$]hPTH(1-34) | 1.54 |
| [Arg$^{16}$,Gln$^{27}$]hPTH(1-34) | 2.16 |
| [Arg$^{26,27}$]hPTH (1-34) | 0.98 |
| [Lys$^{15,16}$,His$^{27}$]hPTH(1-34) | 1.49 |
| [D-Lys$^{16}$]hPTH(1-34) | 0.86 |
| [Lys$^{15,16,17}$,His$^{27}$]hPTH (1-34) | 7.47 |
| [Gln$^{16}$]hPTH(1-34) | 1.73 |
| [Lys$^{16}$,Asp$^{17}$]hPTH(1-34) | 1.24 |
| [Lys$^{15,16,17}$]hPTH (1-34) | 7.62 |
| [Lys$^{16,17}$]hPTH(1-34) | 8.85 |
| [Lys$^{14,15,16,17}$]hPTH (1-34) | 6.39 |
| [Lys$^{16}$]hPTH(1-34) | 5.48 |

What is claimed is:

1. A peptide represented by the amino acid sequence:

Ser—Val—$R_1$—Glu—Ile—Gln—Leu—Met—His—Asn—Leu—Gly—Lys—$R_2$—Met—Glu—Arg—Val—Glu—Trp—Leu—$R_3$—Leu—Gln—Asp—Val—His—Asn—$R_4$ or a salt thereof, wherein $R_1$ represents Ser or a D-α-amino acid residue of 4 or less carbon atoms;

$R_2$ represents a tetrapeptide chain which contains at least one water-soluble α-amino acid residue;

$R_3$ represents a tripeptide chain which contains at least one water-soluble α-amino acid residue; and $R_4$ represents an aromatic acid residue or an amide thereof, with the exclusion of the peptide or salt thereof wherein $R_1$ is Ser, $R_2$ is His-Leu-Asn-Ser, and $R_3$ is E-T-F-G where E is Arg or His, F is Lys or His, and G is Lys, Leu or Gln.

2. A peptide or a salt thereof according to claim 1, wherein $R_1$ is a neutral amino acid residue; $R_2$ is A-B-C-D wherein A represents His or a water-soluble amino acid residue other than His, B represents Leu or a water-soluble amino acid residue; C represents a water-soluble amino acid residue and D represents Ser or a water-soluble amino acid residue;

$R_3$ is a tripeptide chain consisting of basic or neutral water-soluble α-amino acids.

3. A peptide or salt thereof according to claim 2, wherein a basic amino acid residue is a L- or D-α amino acid residue represented by the following formula:

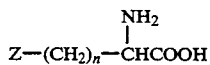

wherein Z represents $NH_2$, —$NHC(NH)NH_2$ or, an imidazole ring, and n represents the integer of 1 to 5.

4. The peptide or a salt thereof according to claim 3 wherein a basic amino acid residue is Lys, Arg or Orn.

5. The peptide or a salt thereof according to claim 1 wherein $R_1$ is Ser, D-Ser or D-Ala.

6. The peptide or a salt thereof according to claim 2 wherein A is His or Lys.

7. The peptide or a salt thereof according to claim 2 wherein B is Leu, Lys or Arg.

8. The peptide or a salt thereof according to claim 2 wherein C is Asn, Orn, Hci, Asp, Arg, Lys, D-Lys, Ser or Gly.

9. The peptide or a salt thereof according to claim 2 wherein D is Ser, Lys, Asp or Arg.

10. The peptide or a salt thereof according to claim 1 wherein $R_2$ is His-Lys-Lys-Lys, His-Leu-Lys-Lys, Lys-Lys-Lys-Lys or His-Leu-Lys-Ser.

11. The peptide or salt thereof according to claim 1 wherein $R_3$ is represented by E'-F'-G' and E' is Arg or Gln.

12. The peptide or salt thereof according to claim 1 wherein $R_3$ is represented by E'-F'-G' and F' is Lys, Gln or Arg.

13. The peptide or a salt thereof according to claim 1 wherein $R_3$ is represented by E'-F'-G' and G' is Lys, Gln, Arg, His, Asn, Thr or Ser.

14. The peptide or a salt thereof according to claim 1 wherein $R_3$ is Arg-Gln-Gln or Arg-Lys-His.

15. The peptide or a salt thereof according to claim 1 wherein $R_4$ is Phe, Phe-$NH_2$, Tyr or Tyr-$NH_2$.

16. The peptide or a salt thereof according to claim 1 wherein (1) $R_1$ is Ser, $R_2$ is His-Lys-Lys-Lys, $R_3$ is Arg-Lys-His, $R_4$ is Phe;

(2) $R_1$ is Ser, $R_2$ is His-Lys-Lys-Lys, $R_3$ is Arg-Lys-Lys, $R_4$ is Phe;

(3) $R_1$ is Ser, $R_2$ is His-Leu-Lys-Lys, $R_3$ is Arg-Lys-Lys, $R_4$ is Phe;

(4) $R_1$ is Ser, $R_2$ is Lys-Lys-Lys-Lys, $R_3$ is Arg-Lys-Lys, $R_4$ is Phe; or (5) $R_1$ is Ser, $R_2$ is His-Leu-Lys-Ser, $R_3$ is Arg-Lys-Lys, $R_4$ is Phe-$NH_2$.

17. The peptide or a salt thereof according to claim 1, wherein $R_1$ is Ser, $R_2$ is His-Lys-Lys, Lys, $R_3$ is Arg-Lys-His, $R_4$ is Phe.

18. The peptide or a salt thereof according to claim 1, wherein $R_1$ is Ser, $R_2$ is His-Lys-Lys-Lys, $R_3$ is Arg-Lys-Lys, $R_4$ is Phe.

19. The peptide or a salt thereof according to claim 1, wherein $R_1$ is Ser, $R_2$ is His-Leu-Lys-Lys, $R_3$ is Arg-Lys-Lys, $R_4$ is Phe.

20. The peptide or a salt thereof according to claim 1, wherein $R_1$ is Ser, $R_2$ is Lys-Lys-Lys-Lys, $R_3$ is Arg-Lys-Lys, $R_4$ is Phe.

21. The peptide or a salt thereof according to claim 1, wherein $R_1$ is Ser, $R_2$ is His-Leu-Lys-Ser, $R_3$ is Arg-Lys-Lys, $R_4$ is Phe-$NH_2$.

22. The peptide or salt thereof according to claim 1 wherein $R_2$ and $R_3$ each contain at least one hydrophilic α-amino acid.

23. The peptide or salt thereof according to claim 1 wherein $R_2$ and $R_3$ each contain at least one naturally occurring hydrophilic α-amino acid.

* * * * *

UNITED STATES PATENT AND TRADEMARK OFFICE
CERTIFICATE OF CORRECTION

PATENT NO. : 5,434,246
DATED : July 18, 1995
INVENTOR(S) : Fukuda et al

It is certified that error appears in the above-indentified patent and that said Letters Patent is hereby corrected as shown below:

Column 11, line 35 (claim 1), please delete "an aromatic acid residue" and insert --an aromatic amino acid residue--.

Column 11, line 38 (claim 1), please delete "E-T-F-G" and insert --E-F-G--.

Column 12, line 49 (claim 17), please delete "His-Lys-Lys,Lys" and insert --His-Lys-Lys-Lys--.

Signed and Sealed this

Seventeenth Day of September, 1996

*Attest:*

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 34 amino acids
      ( B ) TYPE: amino acid
      ( D ) TOPOLOGY: linear ( i i ) MOLECULE TYPE: protein ( v ) FRAGMENT TYPE: N-terminal ( x i ) SEQUENCE DESCRIPTION: SEQ ID NO:1:

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe
```

( 2 ) INFORMATION FOR SEQ ID NO:2:

( i ) SEQUENCE CHARACTERISTICS:
      ( A ) LENGTH: 34 amino acids
      ( B ) TYPE: amino acid
      ( D ) TOPOLOGY: linear ( i i ) MOLECULE TYPE: protein ( v ) FRAGMENT TYPE: N-terminal ( i x ) FEATURE:
      ( B ) LOCATION: 3 Xaa=Ser or D- alpha-amino acid residue of 4 or less carbon atoms, 14 Xaa=His or water-soluble alpha-amino acid, 15 Xaa=Leu or water-soluble alpha-amino acid, 16 Xaa=water-soluble alpha-amino acid,
17 Xaa=Ser or water-soluble alpha-amino acid,
25 Xaa=water-soluble alpha-amino acid, 26 Xaa=water-
soluble alpha-amino acid, 27 Xaa=water-soluble alpha-
amino acid, 34 Xaa=aromatic amino acid or amide thereof (C) IDENTIFICATION METHOD: E (xi) SEQUENCE DESCRIPTION: SEQ ID NO:2:

```
Ser Val Xaa Glu Ile Gln Leu Met His Asn Leu Gly Lys Xaa Xaa Xaa
1             5                   10                      15

Xaa Met Glu Arg Val Glu Trp Leu Xaa Xaa Xaa Leu Gln Asp Val His
            20                  25                  30

Asn Xaa
    34
```